(12) United States Patent
Zhang et al.

(10) Patent No.: US 11,826,523 B2
(45) Date of Patent: Nov. 28, 2023

(54) MAGNETIC NAVIGATION-GUIDED TEAR-AWAY SHEATH FOR CARDIAC CONDUCTION BUNDLE PACING

(71) Applicant: Wuxi People's Hospital, Jiangsu (CN)

(72) Inventors: Changying Zhang, Jiangsu (CN); Shipeng Dang, Jiangsu (CN); Ruxing Wang, Jiangsu (CN); Kulin Li, Jiangsu (CN); Xiaoyu Liu, Jiangsu (CN); Jie Zheng, Jiangsu (CN)

(73) Assignee: Wuxi People's Hospital, Jiangsu (CN)

( * ) Notice: Subject to any disclaimer, the term of this patent is extended or adjusted under 35 U.S.C. 154(b) by 758 days.

(21) Appl. No.: 17/008,644

(22) Filed: Sep. 1, 2020

(65) Prior Publication Data
US 2021/0069472 A1  Mar. 11, 2021

(30) Foreign Application Priority Data
Sep. 6, 2019 (CN) .......................... 201910841634.2

(51) Int. Cl.
*A61M 25/01* (2006.01)
*A61N 1/05* (2006.01)
*A61N 1/37* (2006.01)
*A61N 1/375* (2006.01)

(52) U.S. Cl.
CPC ......... *A61M 25/0127* (2013.01); *A61N 1/056* (2013.01); *A61N 1/3702* (2013.01); *A61N 1/375* (2013.01); *A61M 2025/0166* (2013.01); *A61M 2025/0188* (2013.01)

(58) Field of Classification Search
CPC .......... A61M 25/0127; A61M 25/0668; A61M 2025/0166; A61M 2025/0188; A61N 1/056; A61N 1/375; A61N 1/37512
See application file for complete search history.

(56) References Cited

U.S. PATENT DOCUMENTS

| 4,585,013 | A | * | 4/1986 | Harris | ..................... | A61N 1/056 |
|---|---|---|---|---|---|---|
| | | | | | | 607/126 |
| 5,409,469 | A | * | 4/1995 | Schaerf | ............. | A61M 25/0662 |
| | | | | | | 604/524 |
| 5,441,504 | A | * | 8/1995 | Pohndorf | .......... | A61M 25/0668 |
| | | | | | | 604/167.03 |
| 5,507,751 | A | * | 4/1996 | Goode | ............. | A61B 17/32075 |
| | | | | | | 606/108 |

(Continued)

*Primary Examiner* — Ryan J. Severson
(74) *Attorney, Agent, or Firm* — JCIP GLOBAL INC.

(57) ABSTRACT

The present invention relates to a magnetic navigation-guided tear-away sheath for cardiac conduction bundle pacing, including a sheath body and a joint fixedly connected to a rear end of the sheath body. The sheath body includes a front flexible section and a rear fixed section, and the front flexible section is freely bendable. An outer surface near a head end of the front flexible section is provided with a plurality of pairs of half-ring magnets, two half-ring magnets in each pair of half-ring magnets are symmetrically disposed and form a ring, and a gap is kept between the two half-ring magnets. The head end of the front flexible section is provided with three electrodes uniformly disposed in a circumferential direction, and the three electrodes can be freely combined two by two, to form three electrode pairs used to record and position an intracardiac potential.

9 Claims, 2 Drawing Sheets

(56) References Cited

U.S. PATENT DOCUMENTS

| | | | | |
|---|---|---|---|---|
| 6,277,107 B1* | 8/2001 | Lurie | A61M 25/0054 | 604/528 |
| 6,278,897 B1* | 8/2001 | Rutten | A61N 1/056 | 607/122 |
| 6,733,500 B2* | 5/2004 | Kelley | A61M 25/0147 | 606/41 |
| 6,892,087 B2* | 5/2005 | Osypka | A61N 1/056 | 600/374 |
| 7,091,412 B2* | 8/2006 | Wang | B82Y 25/00 | 607/116 |
| 7,655,014 B2* | 2/2010 | Ko | A61N 1/05 | 606/129 |
| 7,762,995 B2* | 7/2010 | Eversull | A61M 25/1002 | 604/264 |
| 7,840,261 B2* | 11/2010 | Rosenman | A61N 1/056 | 607/2 |
| 8,938,310 B2* | 1/2015 | Spotnitz | A61N 1/056 | 607/125 |
| 2002/0165537 A1* | 11/2002 | Kelley | A61M 25/09 | 606/41 |
| 2003/0083560 A1* | 5/2003 | Osypka | A61N 1/056 | 600/374 |
| 2003/0229386 A1* | 12/2003 | Rosenman | A61N 1/056 | 607/116 |
| 2003/0233115 A1* | 12/2003 | Eversull | A61M 25/1002 | 606/194 |
| 2004/0230271 A1* | 11/2004 | Wang | A61N 1/375 | 607/116 |
| 2006/0122676 A1* | 6/2006 | Ko | A61N 1/056 | 607/116 |
| 2012/0097174 A1* | 4/2012 | Spotnitz | A61N 1/056 | 128/853 |
| 2021/0069472 A1* | 3/2021 | Zhang | A61N 1/056 | |

* cited by examiner

MAGNETIC NAVIGATION-GUIDED TEAR-AWAY SHEATH FOR CARDIAC CONDUCTION BUNDLE PACING

CROSS-REFERENCE TO RELATED APPLICATION

This application claims the priority benefit of China application serial no. 201910841634.2, filed on Sep. 6, 2019. The entirety of the above-mentioned patent application is hereby incorporated by reference herein and made a part of this specification.

TECHNICAL FIELD

The present invention relates to a magnetic navigation-guided tear-away sheath for cardiac conduction bundle pacing, and belongs to the technical field of cardiac pacing and electrophysiology.

BACKGROUND

Artificial cardiac pacing has been clinically applied for over 60 years. With the fast development of bioengineering technology, various new cardiac pacing techniques have emerged. In a conventional cardiac pacing technique, pacemaker leads are commonly tined or screwed into the muscle of heart wall, so that direct electrical signals only travel along the wire and are prevented from traveling to places other than between the pacemaker and heart. In recent years, a new cardiac pacing technique of screwing pacemaker leads into the native conduction system in the heart wall and using the cardiac conduction bundle to restore normal cardiac contraction sequence is drawing more and more attention. Such an artificial cardiac pacing mode is closer to physiological pacing, which reduces the incidence of heart failure and can improve heart function.

At present, the implementation of cardiac conduction bundle pacing has the following difficulties: 1. The cardiac conduction bundle is not directly visible. 2. Electrophysiological anatomy is not identical with tissue anatomy. 3. There are various adjacent tissues around the cardiac conduction bundle. 4. The heart keeps beating. 5. The heart has anatomic variations, structural changes and the like. 6. Surgeons have different habits, techniques, dexterity, and so on. Due to these difficulties, with the help of existing surgical tools, the cardiac conduction bundle pacing still has problems such as low success rate, long learning curve and long procedure time.

It is found that one of the major causes for the above problems in the cardiac conduction bundle pacing is that the existing sheath for implanting pacemaker leads is not advanced enough. Preformed sheath and bendable sheath can provide different support but have limited adjustment ranges and relatively low precision. It is inconvenient to control the angle and depth in the process of screwing pacemaker leads. There is a risk of myocardial perforation if the pacemaker leads are screwed excessively deep. Improper lead entry angle may cause pacing failure, damage to other tissues and even dislocation of the pacemaker leads. In the case of cardiac dilatation or anatomic variation, the potential of the cardiac conduction system may not be found in the conventional anatomic area.

SUMMARY

An objective of the present invention is to provide a magnetic navigation-guided tear-away sheath for cardiac conduction bundle pacing to overcome the deficiencies in the prior art, and the sheath has a delicate structure and a proper design and can be conveniently used.

According to a technical solution provided in the present invention: A magnetic navigation-guided tear-away sheath for cardiac conduction bundle pacing includes a sheath body and a joint fixedly connected to a rear end of the sheath body, a one-way anti-leak valve being provided inside the joint, and the sheath body being hollow inside, where the sheath body includes a front flexible section and a rear fixed section that are integrally formed, and the front flexible section is freely bendable; an outer surface near a head end of the front flexible section is provided with a plurality of pairs of half-ring magnets, two half-ring magnets in each pair of half-ring magnets are symmetrically disposed and form a ring, and a gap for an incision knife to pass through is kept between the two half-ring magnets; the head end of the front flexible section is further provided with three electrodes uniformly disposed in a circumferential direction, the three electrodes can be freely combined two by two, to form three electrode pairs, the three electrode pairs are capable of recording three local double-electrode potentials of the heart and are used to record and position an intracardiac potential; and each electrode is connected to one electrode lead, the electrode lead is embedded in a wall of the sheath body in a length direction of the sheath body, a position near a tail end of the sheath body is provided with an electrode tail interface, and the other end of each of the three electrode leads is fixedly disposed in the electrode tail interface.

As a further improvement of the present invention, the front flexible section has a length of 6 cm to 8 cm and an inner diameter greater than or equal to 1.88 mm.

As a further improvement of the present invention, the rear fixed section has a length of 35 cm to 45 cm and an inner diameter greater than or equal to 1.88 mm.

As a further improvement of the present invention, an outer wall of the sheath body is provided with an incision guidewire, a tail end of the joint is provided with an incision guide hole corresponding to a rear end of the incision guidewire, and a front end of the incision guidewire passes through the gap between the two half-ring magnets.

As a further improvement of the present invention, a side wall of the joint is further connected to a liquid inlet pipe, a rear end of the liquid inlet pipe is a liquid inlet port, and a front end of the liquid inlet pipe is in communication with the interior of the joint.

As a further improvement of the present invention, there are two to four pairs of half-ring magnets.

As a further improvement of the present invention, the plurality of pairs of half-ring magnets are uniformly disposed at equal intervals on the outer surface of the front flexible section.

As a further improvement of the present invention, the material of the front flexible section is a biocompatible polymer material, and the material of the electrode is a biocompatible noble metal material.

As a further improvement of the present invention, the surface of the electrode preferably has a smooth arc-shape.

Compared with the prior art, the present invention has the following advantages:

1). The present invention has a delicate structure and a proper design. A front flexible section is provided with a plurality of pairs of half-ring magnets, so that the front flexible section is freely bendable in an external magnetic field environment (magnetic navigation system) to adjust direction and angle, and it is convenient to find conduction system potential. In addition, the present invention facilitates contact with a cardiac chamber and stable attachment to an endocardium, to ensure that pacemaker leads are stably screwed into the cardiac conduction bundle. A head end of the front flexible section is provided with three electrodes. The three electrodes can be freely combined two by two, to form three electrode pairs. The three electrode pairs are capable of recording three local double-electrode potentials of the heart and are used to record and position an intracardiac potential.

2). In the present invention, a contrast agent may be injected through a liquid inlet port of a liquid inlet pipe, to facilitate imaging to show an endocardium.

3). In the present invention, an incision guidewire is disposed, and a front end of the incision guidewire passes through a gap between two half-ring magnets. Such a conventional incision knife can accurately cut open a sheath body without being hindered by the half-ring magnets, so that it is convenient to remove a sheath.

DETAILED DESCRIPTION OF EMBODIMENTS

Figure 1:
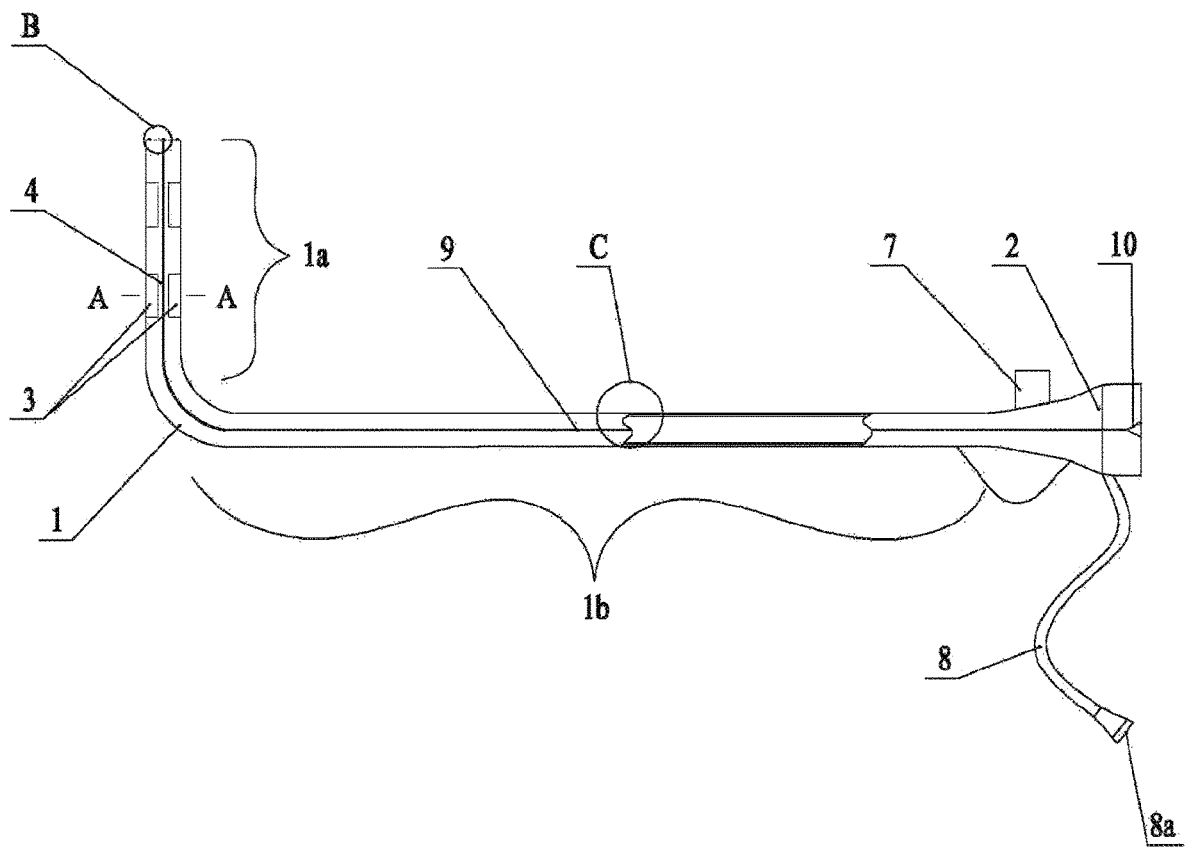
FIG. 1 is a schematic diagram of an overall structure according to an embodiment of the present invention.
Figure 2:
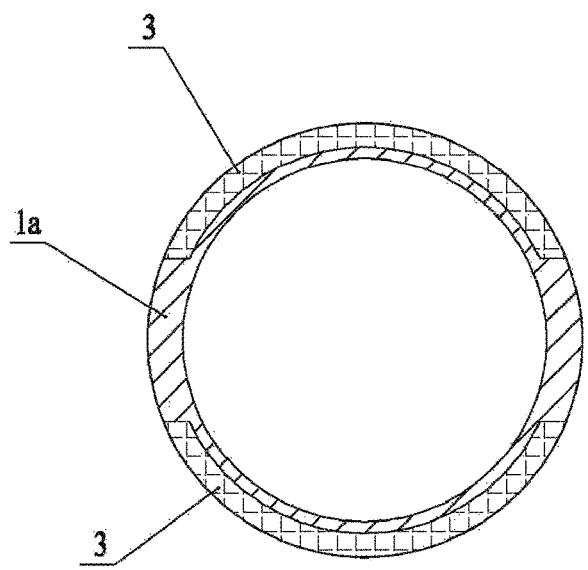
FIG. 2 is a schematic enlarged sectional view of a surface A-A in FIG. 1.
Figure 3:
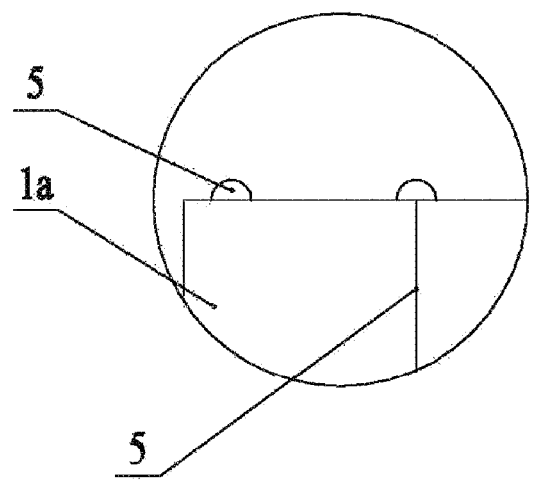
FIG. 3 is a schematic enlarged view of a portion B in FIG. 1.
Figure 4:
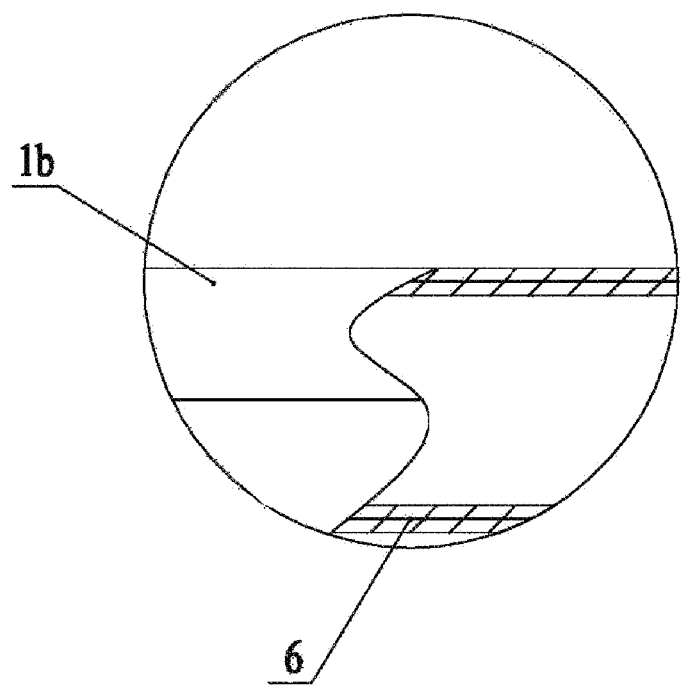
FIG. 4 is a schematic enlarged view of a portion C in FIG. 1.

The present invention is further described below with reference to the specific accompanying drawings and embodiments.

As shown in FIG. 1 to FIG. 4, an embodiment discloses a magnetic navigation-guided tear-away sheath for cardiac conduction bundle pacing, including a sheath body 1 and a joint 2 fixedly connected to a rear end of the sheath body. A one-way anti-leak valve is provided inside the joint 2, and the sheath body 1 is hollow inside. The sheath body 1 includes a front flexible section 1a and a rear fixed section 1b that are integrally formed, and the front flexible section 1a is freely bendable. An outer surface near a head end of the front flexible section 1a is provided with a plurality of pairs of half-ring magnets 3, two half-ring magnets 3 in each pair of half-ring magnets 3 are symmetrically disposed and form a ring, and a gap 4 for an incision knife to pass through is kept between the two half-ring magnets 3. The head end of the front flexible section 1a is further provided with three electrodes 5 uniformly disposed in a circumferential direction, each electrode 5 is connected to one electrode lead 6, the electrode lead 6 is embedded in a wall of the sheath body 1 in a length direction of the sheath body 1, a position near a tail end of the sheath body 1 is provided with an electrode tail interface 7, and the other end of each of the three electrode leads 6 is fixedly disposed in the electrode tail interface 7.

During specific use, a sheath is first implanted in a conventional manner. The front flexible section 1a of the sheath is provided with the plurality of pairs of half-ring magnets 3. Therefore, such a front flexible section 1a is freely bendable in an external magnetic field environment (magnetic navigation system), and magnetic navigation is used to adjust direction and angle of front flexible section 1a, so that it is convenient to find the potential of the cardiac conduction system. The sheath facilitates contact with a cardiac chamber and stable attachment to an endocardium, to ensure that pacemaker leads are stably screwed into the cardiac conduction bundle. With the precision improved, myocardial perforation can also be effectively avoided, procedure time can be reduced, surgical risks can be reduced, and procedure success rate can be increased. The three electrodes 5 can be freely combined two by two, to form three electrode pairs. The three electrode pairs are capable of recording three local double-electrode potentials of the heart and are used to record and position an intracardiac potential.

As shown in FIG. 1, in this embodiment, a side wall of the joint 2 is further connected to a liquid inlet pipe 8, and a rear end of the liquid inlet pipe 8 is a liquid inlet port 8a. A front end of the liquid inlet pipe 8 is in communication with the interior of the joint 2. With such an arrangement, a contrast agent may be injected through the liquid inlet port 8a, to facilitate imaging to show an endocardium and implement convenient operations.

As shown in FIG. 1, in this embodiment, the outer surface of the front flexible section 1a is provided with two pairs of half-ring magnets 3. During actual production, two to four pairs of half-ring magnets 3 may be disposed, and the plurality of pairs of half-ring magnets 3 are uniformly disposed at equal intervals on the outer surface of the front flexible section 1a. With such an arrangement, it can be ensured that the front flexible section 1a can be flexibly bent under magnetic navigation.

In the present invention, the length of the sheath body 1 may be flexibly disposed. Generally, the front flexible section 1a has a length of 6 cm to 8 cm and the rear fixed section 1b has a length of 35 cm to 45 cm, and both the front flexible section 1a and the rear fixed section 1b have an inner diameter greater than or equal to 1.88 mm. With such an arrangement, the front flexible section 1a has a sufficient length to bend, and all clinical requirements can basically be satisfied.

As shown in FIG. 1, in this embodiment, an outer wall of the sheath body 1 is provided with an incision guidewire 9, a tail end of the joint 2 is provided with an incision guide hole 10 corresponding to a rear end of the incision guidewire 9, and a front end of the incision guidewire 9 passes through the gap 4 between the two half-ring magnets 3. With such an arrangement, a conventional incision knife can be used to accurately cut open the sheath body 1 without being hindered by the half-ring magnets 3, so that it is convenient to remove a sheath.

In the present invention, the material of the front flexible section 1a is preferably a biocompatible polymer material, for example, polyether block amide, polyurethane or a nylon material. The material of the electrode 5 is preferably a biocompatible noble metal material, for example, a platinum-iridium alloy. The half-ring magnets 3 is made of a permanent magnetic material such as a neodymium-iron-boron alloy material or a ferrite material with relatively high remanence. Both the half-ring magnets 3 and the electrode 5 may be fixedly bonded on the front flexible section 1a with a medical adhesive. The medical glue may be 4011, 4014, 3011 or the like.

In the present invention, the surface of the electrode 5 preferably has a smooth arc-shape. With such an arrangement, a cardiac chamber is prevented from scratching to achieve protection.

The foregoing descriptions are only preferred embodiments of the present invention, and the foregoing specific embodiments are not intended to limit the present invention. Various variations and modifications may be made within the scope of the technical concept of the present invention. Any variation, modification or equivalent replacement made by a person of ordinary skill in the art according to the foregoing description falls within the protection scope of the present invention.

What is claimed is:

1. A magnetic navigation-guided tear-away sheath for cardiac conduction bundle pacing, comprising a sheath body and a joint fixedly connected to a rear end of the sheath body, a one-way anti-leak valve being provided inside the joint, and the sheath body being hollow inside, wherein the sheath body comprises a front flexible section and a rear fixed section that are integrally formed, and the front flexible section is freely bendable; an outer surface near a head end of the front flexible section is provided with a plurality of pairs of half-ring magnets, two half-ring magnets in each of the pairs of the half-ring magnets are symmetrically disposed and form a ring, and a gap for an incision knife to pass through is kept between the two half-ring magnets; the head end of the front flexible section is further provided with three electrodes uniformly disposed in a circumferential direction, the three electrodes are capable of being freely combined two by two, to form three electrode pairs, and the three electrode pairs are capable of recording three local double-electrode potentials of heart and are used to record and position an intracardiac potential; and each of the electrodes is connected to one of electrode leads, the electrode leads are embedded in a wall of the sheath body in a length direction of the sheath body, a position near a tail end of the sheath body is provided with an electrode tail interface, and one end of each of the electrode leads is fixedly disposed in the electrode tail interface.

2. The magnetic navigation-guided tear-away sheath for cardiac conduction bundle pacing according to claim 1, wherein the front flexible section has a length of 6 cm to 8 cm and an inner diameter greater than or equal to 1.88 mm.

3. The magnetic navigation-guided tear-away sheath for cardiac conduction bundle pacing according to claim 1, wherein the rear fixed section has a length of 35 cm to 45 cm and an inner diameter greater than or equal to 1.88 mm.

4. The magnetic navigation-guided tear-away sheath for cardiac conduction bundle pacing according to claim 1, wherein an outer wall of the sheath body is provided with an incision guidewire, a tail end of the joint is provided with an incision guide hole corresponding to a rear end of the incision guidewire, and a front end of the incision guidewire passes through the gap between the two half-ring magnets.

5. The magnetic navigation-guided tear-away sheath for cardiac conduction bundle pacing according to claim 1, wherein a side wall of the joint is further connected to a liquid inlet pipe, a rear end of the liquid inlet pipe is a liquid inlet port, and a front end of the liquid inlet pipe is in communication with an interior of the joint.

6. The magnetic navigation-guided tear-away sheath for cardiac conduction bundle pacing according to claim 1, wherein number of the pairs of the half-ring magnets are two to four.

7. The magnetic navigation-guided tear-away sheath for cardiac conduction bundle pacing according to claim 1, wherein the pairs of half-ring magnets are uniformly disposed at equal intervals on the outer surface of the front flexible section.

8. The magnetic navigation-guided tear-away sheath for cardiac conduction bundle pacing according to claim 1, wherein a material of the front flexible section is a biocompatible polymer material, and a material of the electrode is a biocompatible noble metal material.

9. The magnetic navigation-guided tear-away sheath for cardiac conduction bundle pacing according to claim 1, wherein a surface of each of the electrodes has a smooth arc-shape.

* * * * *